US00PP25691P3

(12) United States Plant Patent

Scalzo et al.

(10) Patent No.: US PP25,691 P3
(45) Date of Patent: Jul. 14, 2015

(54) BLUEBERRY PLANT NAMED 'CIPRIA'

(50) Latin Name: *Vaccinium corymbosum*
Varietal Denomination: Cipria

(71) Applicant: The New Zealand Institute for Plant and Food Research Limited, Auckland (NZ)

(72) Inventors: Jessica Scalzo, Havelock North (NZ); Narandra Patel, Hamilton (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 13 days.

(21) Appl. No.: 13/815,549

(22) Filed: Mar. 8, 2013

(65) Prior Publication Data

US 2013/0347151 P1 Dec. 26, 2013

Related U.S. Application Data

(60) Provisional application No. 61/664,155, filed on Jun. 26, 2012.

(51) Int. Cl.
*A01H 5/08* (2006.01)
*A01H 5/00* (2006.01)

(52) U.S. Cl.
USPC ..... Plt./157
CPC ..... *A01H 5/00* (2013.01)

(58) Field of Classification Search
USPC ..... Plt./157
CPC ..... A01H 5/08; A01H 5/0887; A01H 5/00
See application file for complete search history.

(56) References Cited

U.S. PATENT DOCUMENTS

| | | | |
|---|---|---|---|
| PP20,515 | P3 | 12/2009 | Patel |
| PP21,720 | P3 | 2/2011 | Patel |
| PP21,721 | P3 | 2/2011 | Patel |
| PP21,735 | P3 | 3/2011 | Patel |
| PP21,736 | P3 | 3/2011 | Patel |
| PP21,761 | P3 | 3/2011 | Patel |
| PP21,881 | P3 | 4/2011 | Patel |

*Primary Examiner* — June Hwu
(74) *Attorney, Agent, or Firm* — Lathrop & Gage LLP

(57) ABSTRACT

A new and distinct blueberry variety is described. The variety results from selection among a population of seedlings derived from the deliberate open pollination of the variety 'Summit' (not patented). The new variety is distinguished from others by the fruit harvest season, fruit size, flavour and bloom, along with the plant habit. Fruit of 'Cipria' is medium to large in size with a strong bloom; the mature plant has a semi-upright to spreading habit.

2 Drawing Sheets

Genus and species of plant claimed: *Vaccinium corymbosum.*

Variety denomination: 'Cipria'.

BACKGROUND TO THE INVENTION

A plant variety named 'RH48' was selected from among a population of seedlings derived from the open pollination of the variety 'Summit' (not patented), located at Ruakura, Hamilton, New Zealand. Along with a number of other selections 'RH48' was identified as having potential for test and evaluation and was shipped to Gilten, Germany in 2001. In 2002 it was identified as having potential as a new variety and was asexually propagated. The resulting plants were planted out at Gilten and were subsequently found to be true to type demonstrating that the characteristics of the new variety are stable and transmitted without change through succeeding generations. Asexual propagation has since been carried out through both soft and hard wood cuttings at Gilten, Germany. 'RH48' was later designated 'Cipria'. 'Cipria' differs from its known parent 'Summit' as the plant habit of 'Cipria' is semi-upright to spreading while 'Summit' is more upright.

SUMMARY OF THE INVENTION

'Cipria' is characterised by its early to mid season harvest maturity, medium to large fruit size, small pedicel scar, strong bloom, and semi-upright to spreading habit. 'Cipria' is distinguished from a number of other varieties by the following characteristics:

'Cipria' has a semi-upright to spreading habit while 'Island Blue' (not patented) and 'Mondo' (not patented) have an upright habit.

'Cipria' produces oblate medium to large fruit, averaging 2.2 g, with a strong bloom, whereas 'Nui' (U.S. Plant Pat. No. 6,699) produces flat large fruit, averaging 3 g, with medium boom and lower soluble solid content, under the same conditions in Germany.

DETAILED DESCRIPTION

Figure 1:
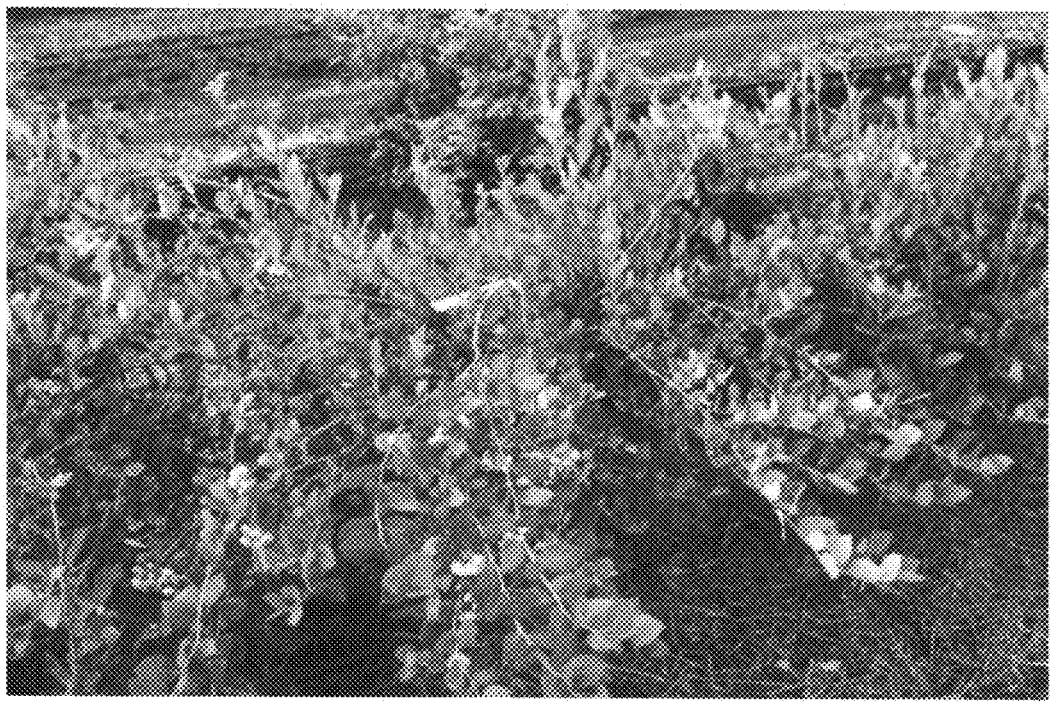
FIG. 1 shows mature, seven year old, 'Cipria' plants with fruit.
Figure 2:
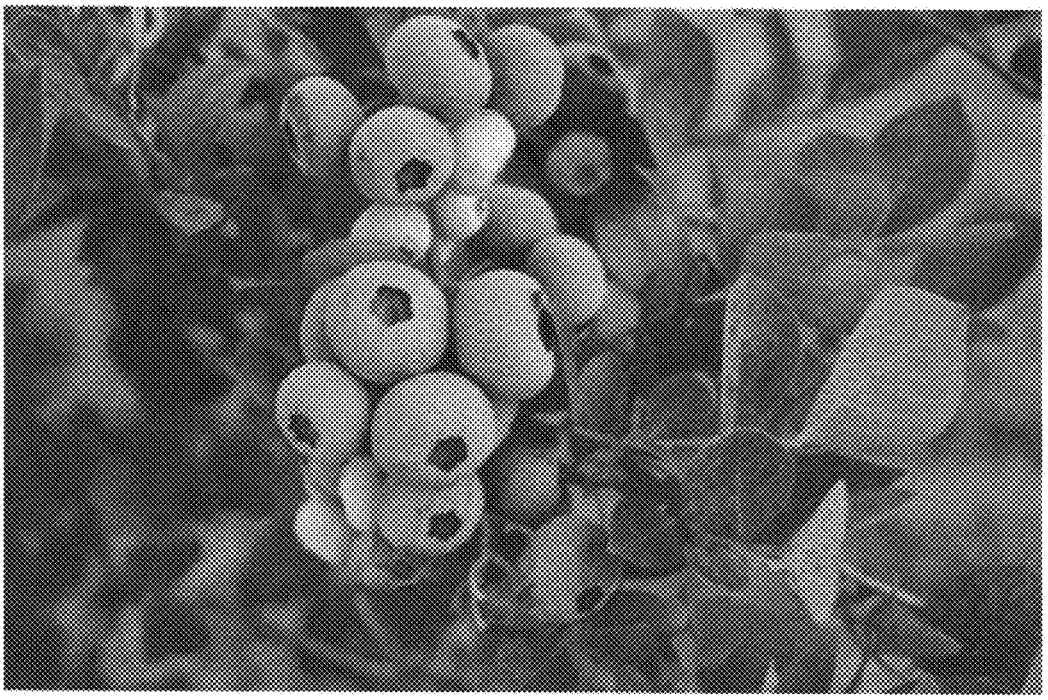
FIG. 2 shows fruit of 'Cipria' on the plant.

The following is a description of the new variety with color terminology in accordance with The Royal Horticultural Society Colour Charts (R.H.S.C.C.) 2001 edition.

Observations were made on specimens grown at Gilten, Germany and at Ruakura, Hamilton, New Zealand. The observations were made in the 2010-2014 seasons on 6-9 year old bushes.

Plant and foliage:

*Plant*.—Medium size at maturity, with average plant height 1.6 m and canopy diameter 2.1 m, managed under standard orchard practice. Growth habit is semi-upright to spreading and fruit are borne only on one-year-old shoots. Surface texture of six month old stems is smooth at dormancy and colour is yellow green 146D.

*Leaves*.—Mature fully expanded leaves are medium to short at an average of approximately 52.0 mm long and 32.4 mm wide. The pinnate leaves are oblate in shape with smooth margins. The leaves are coloured near green 137A with very low and uniform glossiness on the upper surface. On the underside the leaves are coloured near green 138C with venation coloured near red purple 60A. The petioles are an average of approximately 3.5 mm long and are coloured near yellow green 145B.

Inflorescence: Flowers were an average of approximately 7.3 mm long and 7.2 mm wide with very weak anthocyanin in the petals which are coloured near white 155C. The flower shape is urceolate. The ovary is inferior and the petals are fused into a corolla tube with 5 lobes. The corolla aperture diameter has an average diameter of 4.7 mm and the corolla tube has an average diameter of 6.5 mm. The surface texture of the corolla is smooth and the corolla colour is near white 155C. The tip of the style is level with the corolla tip. Pollen colour is near greyed-yellow 161D. The calyx has an average diameter of 6 mm and the calyx colour is near yellow-green 144B. The average number of flowers per cluster is 10.

Fruit:

*Immature fruit*.—Coloured near yellow green 144C to 144D.

*Mature fruit*.—Medium to large in size, with an average fresh weight of 2.2 g and diameter of 17.2 mm. The fruit have a medium to soft firmness under New Zealand conditions and medium firmness in Germany — influenced by environmental conditions. The fruit have a strong bloom. The colour of the fruit with bloom is near violet blue 95D and after bloom has been removed is near violet blue 92C. The fruit are generally oblate in shape with a small dry scar and an average brix of 12.2%. The berry cluster is dense with the average number of berries per cluster, 7. The average diameter of the calyx is 5.3 mm with an average depth of calyx basin 1.2 mm and the calyx aperture shape on the ripe berry is round. The flesh colour of ripe fruit is near greyed green 194C. Fruit harvested and stored for a period of 4 weeks in Motueka, New Zealand maintained good fruit quality.

*Seeds*.—There is an average of between 18 to 32 seeds per fruit with an average length of 1.8 mm, coloured near greyed-orange 175A.

Events: The timing of the beginning of flowering is early compared to standard *V. corymbosum* varieties, while the timing of the beginning of fruit ripening is early to medium. Under New Zealand conditions 50% of flowering occurs late August and 50% of fruit ripening occurs mid December.

Pest and disease: 'Cipria' does not appear particularly resistant or susceptible to any particular pests or diseases known to afflict *V. corymbosum*.

Hardiness: The plant cold hardiness according to the American zone classification has not been determined. 'Cipria' has a chilling requirement of between 600-800 hours.

The invention claimed is:

1. A new and distinct blueberry plant substantially as illustrated and described herein.

* * * * *